US012114999B2

(12) United States Patent
Takahashi et al.

(10) Patent No.: US 12,114,999 B2
(45) Date of Patent: Oct. 15, 2024

(54) ORAL TOOL

(71) Applicant: Murata Manufacturing Co., Ltd., Nagaokakyo (JP)

(72) Inventors: Tomoki Takahashi, Nagaokakyo (JP); Jun Takagi, Nagaokakyo (JP); Hiroaki Togashi, Nagaokakyo (JP); Hiroki Achiwa, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 776 days.

(21) Appl. No.: 17/328,325

(22) Filed: May 24, 2021

(65) Prior Publication Data

US 2021/0386369 A1    Dec. 16, 2021

(30) Foreign Application Priority Data

Jun. 10, 2020   (JP) .................................. 2020-100628

(51) Int. Cl.
*A61B 5/00* (2006.01)

(52) U.S. Cl.
CPC ............ *A61B 5/4875* (2013.01); *A61B 5/682* (2013.01); *A61B 2560/04* (2013.01)

(58) Field of Classification Search
CPC ... A61B 5/4875; A61B 5/682; A61B 2560/04; A61B 5/4277; A61B 2562/029; A61B 2562/247; A61B 10/0051
See application file for complete search history.

(56) References Cited

U.S. PATENT DOCUMENTS

| | | | | |
|---|---|---|---|---|
| 8,734,341 B2* | 5/2014 | Howell | ................ | A61B 5/4875 |
| | | | | 424/9.1 |
| 9,968,777 B1* | 5/2018 | Demarest | ................ | A61B 5/682 |
| 10,258,278 B2* | 4/2019 | Howell | ................ | A61B 5/4277 |
| 10,602,929 B1* | 3/2020 | McKay | ................ | A61B 5/6806 |
| 10,736,612 B2* | 8/2020 | Donovan | ................ | A61B 5/682 |
| 11,013,461 B2* | 5/2021 | Howell | ................ | A61B 5/01 |
| 11,026,664 B1* | 6/2021 | Petrovic | ........... | G01N 33/56983 |
| 11,529,093 B2* | 12/2022 | Furukawa | ............ | A61B 5/4277 |
| 11,666,278 B1* | 6/2023 | McKay | ................ | A63B 71/085 |
| | | | | 700/91 |
| 11,744,779 B1* | 9/2023 | McGrattan | ........... | A61B 5/4205 |
| | | | | 600/590 |
| 2005/0234365 A1* | 10/2005 | Sonis | ..................... | A61B 5/682 |
| | | | | 600/547 |
| 2006/0020179 A1* | 1/2006 | Anderson | .............. | A61B 5/682 |
| | | | | 600/549 |

(Continued)

FOREIGN PATENT DOCUMENTS

| CN | 105914694 A | 8/2016 |
|---|---|---|
| CN | 108720953 A | 11/2018 |

(Continued)

*Primary Examiner* — May A Abouelela
(74) *Attorney, Agent, or Firm* — ArentFox Schiff LLP

(57) ABSTRACT

An oral tool is provided that includes a body, a measurement unit, and a flow stopper. The measurement unit is moveable relative to the body, and includes a sensor unit at an end opposite to an end where the body is disposed. The sensor unit is constructed to be insertable into a mouth. Moreover, the flow stopper is disposed between the measurement unit and the body, and has a surface with a curvature different from a curvature of a surface of the measurement unit.

18 Claims, 5 Drawing Sheets

(56) References Cited

U.S. PATENT DOCUMENTS

| | | | |
|---|---|---|---|
| 2007/0048224 A1* | 3/2007 | Howell | A61B 5/6802 424/9.1 |
| 2012/0203128 A1* | 8/2012 | Levison | A61B 5/6819 600/537 |
| 2012/0289863 A1* | 11/2012 | Goldstein | A61B 10/0051 600/573 |
| 2013/0006068 A1* | 1/2013 | Gemer | A61B 10/0051 600/314 |
| 2013/0211270 A1* | 8/2013 | St. Laurent | A61B 5/682 600/595 |
| 2014/0018641 A1* | 1/2014 | Yoshino | A61B 5/7275 600/301 |
| 2014/0364758 A1* | 12/2014 | Schindhelm | A61B 5/14532 128/204.22 |
| 2015/0196251 A1* | 7/2015 | Outwater | A61B 5/14551 600/324 |
| 2015/0216471 A1* | 8/2015 | Goldstein | A61B 5/682 600/573 |
| 2015/0217614 A1 | 8/2015 | Aoki | |
| 2015/0306486 A1* | 10/2015 | Logan | A61B 5/01 600/549 |
| 2016/0029963 A1* | 2/2016 | Hyde | A61B 7/003 600/300 |
| 2016/0120468 A1* | 5/2016 | Mathew | A61B 5/082 600/301 |
| 2016/0135728 A1 | 5/2016 | Furukawa et al. | |
| 2016/0150981 A1* | 6/2016 | Baker | A61B 5/0878 600/479 |
| 2016/0150995 A1* | 6/2016 | Ratto | A61B 5/4875 600/532 |
| 2016/0262694 A1* | 9/2016 | Calcano | G01L 5/00 |
| 2017/0290545 A1* | 10/2017 | Zerick | A61B 5/742 |
| 2017/0347956 A1* | 12/2017 | Zegarelli | A61B 5/01 |
| 2018/0000378 A1* | 1/2018 | Viertio-Oja | A61B 5/0803 |
| 2018/0000563 A1* | 1/2018 | Shanjani | H04B 5/77 |
| 2018/0280176 A1* | 10/2018 | Longley | A61B 13/00 |
| 2018/0296442 A1* | 10/2018 | Paz | A61M 15/0065 |
| 2019/0183407 A1* | 6/2019 | Furukawa | A61B 5/0537 |
| 2019/0192259 A1* | 6/2019 | Kopelman | A61B 5/682 |
| 2019/0246976 A1* | 8/2019 | Howell | A61B 5/443 |
| 2019/0261889 A1* | 8/2019 | White | A61B 5/682 |
| 2020/0163587 A1* | 5/2020 | Bhattacharjee | A61B 5/085 |
| 2020/0303044 A1* | 9/2020 | Stephen | G06K 7/10722 |
| 2020/0345536 A1* | 11/2020 | Letizia | A61B 5/4557 |
| 2020/0375528 A1* | 12/2020 | Flanagan | A61B 5/087 |
| 2021/0022840 A1* | 1/2021 | Deane | A61C 19/04 |
| 2021/0161633 A1* | 6/2021 | Makin | A61C 19/04 |
| 2021/0204917 A1* | 7/2021 | Wu | A61B 5/1486 |
| 2021/0282665 A1* | 9/2021 | White | A61B 5/742 |
| 2021/0307732 A1* | 10/2021 | Farquar | A61B 5/4845 |
| 2022/0007961 A1* | 1/2022 | Funch-Nielsen | A61B 5/097 |
| 2022/0008243 A1* | 1/2022 | Osorio Martini | A61B 5/0008 |
| 2022/0202169 A1* | 6/2022 | Chan | G16H 40/40 |

FOREIGN PATENT DOCUMENTS

| | | |
|---|---|---|
| JP | S59132115 U | 9/1984 |
| JP | H04136314 U | 12/1992 |
| JP | H07327937 A | 12/1995 |
| JP | H111913 A | 1/1999 |
| JP | 2012075733 A | 4/2012 |
| JP | 2014037844 A | 2/2014 |
| WO | 2004028359 A1 | 4/2004 |
| WO | 2012046567 A1 | 4/2012 |
| WO | 2015125222 A1 | 8/2015 |

* cited by examiner

ORAL TOOL

CROSS REFERENCE TO RELATED APPLICATIONS

The present application claims priority to Japanese Application No. 2020-100628, filed on Jun. 10, 2020, the entire contents of which are incorporated herein by reference.

FIELD OF THE INVENTION

The present invention relates to an oral tool including a sensor unit that is to be inserted into the mouth or brought into contact with the tongue for measurement of various parameters.

BACKGROUND

Currently, WO 2004/28359 discloses a moisture measuring device that can be inserted into the mouth at its distal end to detect moisture in the mouth.

However, saliva of a subject adheres to the moisture measuring device at a portion inserted into the mouth, and, when the device is removed from the mouth, the saliva may flow to the body of the device gripped by a measuring operator and adhere to the hand of the measuring operator, which is not hygienically preferable.

SUMMARY OF THE INVENTION

Accordingly, exemplary embodiments of the present invention provide a hygienic oral tool that at least partially prevents saliva of a subject from flowing to a body of the oral tool gripped by a measuring operator when the oral tool is removed from the mouth.

According to exemplary preferred embodiments, an oral tool is provided that includes a body and a measurement unit connected to the body and including a sensor unit at an end opposite to an end where the body is disposed. Moreover, the sensor unit is constructed to be insertable into the mouth, and a flow stopper is disposed between the measurement unit and the body and has a surface with a curvature different from a curvature of a surface of the measurement unit.

The oral tool according to an exemplary aspect includes the flow stopper disposed between the measurement unit and the body and has a surface with a curvature different from a surface of the measurement unit. Thus, the oral tool at least partially prevents saliva of a subject from flowing to the body of the oral tool gripped by a measuring operator when the oral tool is removed from the mouth.

Additional features, elements, characteristics and advantages of the exemplary embodiments of the present invention will become more apparent from the following detailed description of the present invention with reference to the attached drawings.

DETAILED DESCRIPTION OF THE EMBODIMENTS

An oral tool of a first exemplary aspect includes a body and a measurement unit connected to the body and including a sensor unit at an end opposite to an end where the body is disposed. Moreover, the sensor unit is constructed to be insertable into the mouth, and a flow stopper is disposed between the measurement unit and the body and has a surface with a curvature different from a curvature of a surface of the measurement unit.

The above structure at least partially prevents saliva from flowing from the measurement unit.

In an oral tool of a second exemplary aspect, the flow stopper can be a water-repellent member.

In an oral tool of a third exemplary aspect, the flow stopper can be a deformable soft member.

In an oral tool of a fourth exemplary aspect, the flow stopper can be deformed in accordance with movement of the measurement unit.

In an oral tool of a fifth exemplary aspect, the flow stopper can have a shape of a guard facing toward the measurement unit.

In an oral tool of a sixth exemplary aspect, the flow stopper can have a gap between the measurement unit and the body.

In an oral tool of a seventh exemplary aspect, the flow stopper can be formed from a material selected from a group consisting of natural rubber, styrene-butadiene rubber, chloroprene rubber, acrylonitrile rubber, butyl rubber, ethylene-propylene rubber, silicone rubber, and thermoplastic polyurethane.

In this structure, the material forming the flow stopper less easily hydrolyzes, has static physical properties, and is thus durable for long-term use.

In an oral tool of an eighth exemplary aspect, the flow stopper can have a convex or concave shape to extend along a circumference of a portion between the body and the measurement unit.

In an oral tool of a ninth exemplary aspect, the flow stopper can be constructed to serve as a buffer member disposed between the body and the measurement unit, and the body or the measurement unit can further include a protruding longitudinal rib that comes into contact with the flow stopper.

An oral tool according to exemplary embodiments will now be described below with reference to the attached drawings. Substantially the same components are denoted with the same reference signs throughout the drawings.

First Exemplary Embodiment

Figure 1:
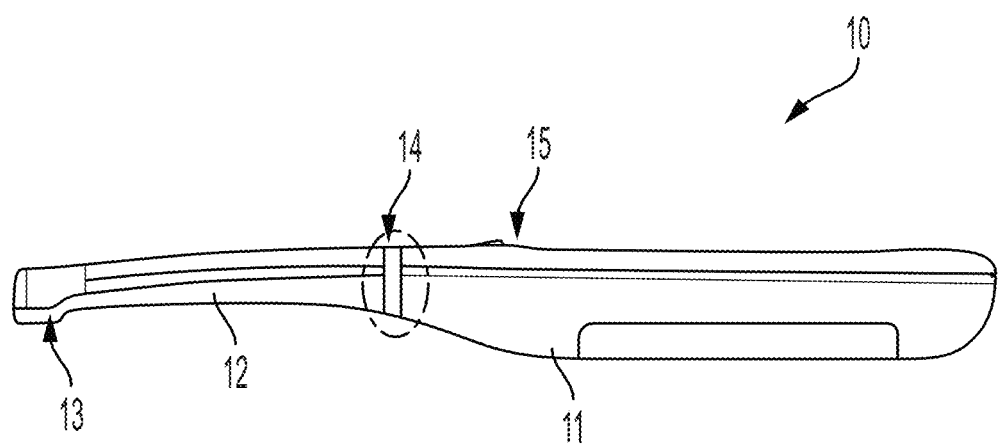
FIG. 1 is a schematic diagram of the appearance of an oral tool according to a first exemplary embodiment.
Figure 2:
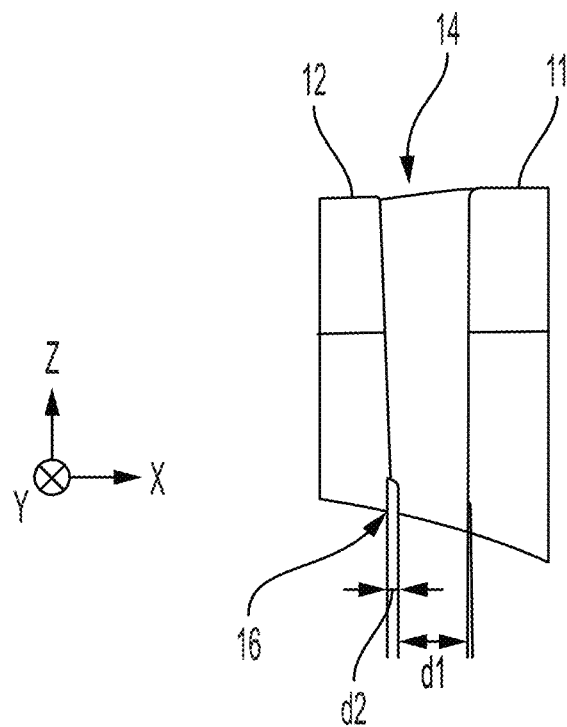
FIG. 2 is an enlarged schematic diagram of a flow stopper disposed at the boundary between a measurement unit and a body.
Figure 3:
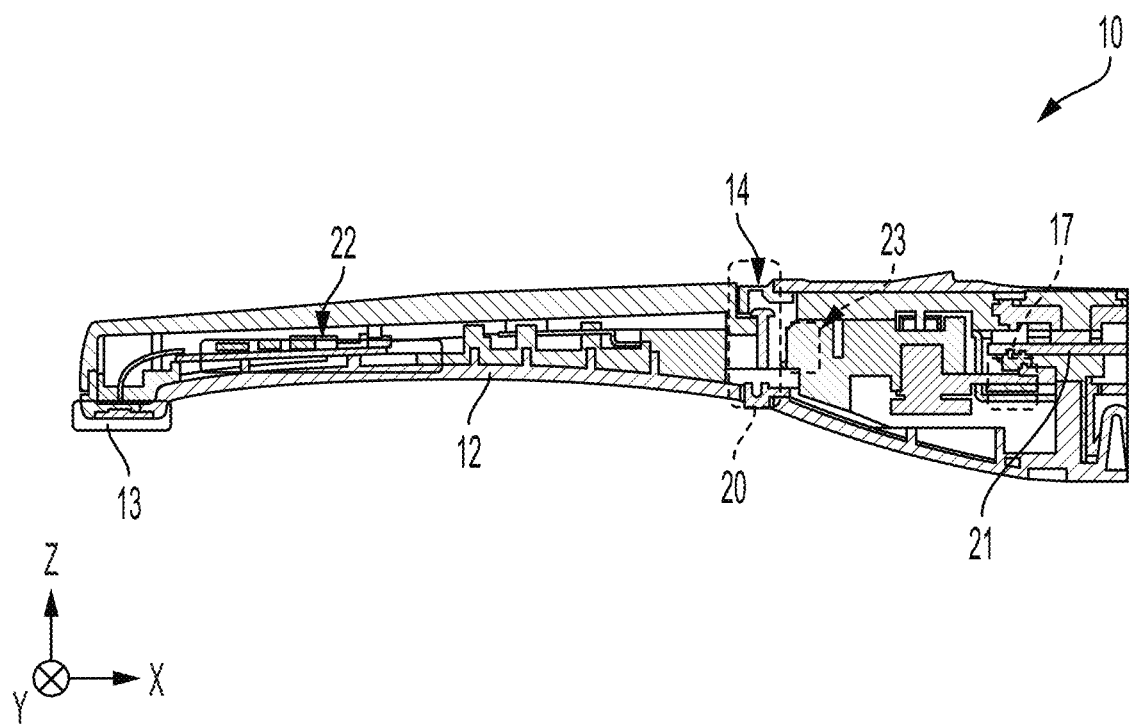
FIG. 3 is a cross-sectional view showing the cross-sectional structure including the flow stopper disposed at the boundary between the measurement unit and the body.

FIG. 1 is a schematic diagram of the appearance of an oral tool 10 according to a first exemplary embodiment. FIG. 2 is an enlarged schematic diagram of a flow stopper 14 disposed at the boundary between a measurement unit 12 and a body 11. FIG. 3 is a cross-sectional view showing the cross-sectional structure including the flow stopper 14 disposed at the boundary between the measurement unit 12 and the body 11. For convenience, the direction in which the measurement unit 12 extends from the body 11 is denoted with a −x direction, the vertical direction is denoted with a z direction, and the depth direction of the drawing sheet is denoted with a y direction.

As shown, the oral tool 10 includes the body 11, the measurement unit 12, and the flow stopper 14. The measurement unit 12 is disposed to be moveably (e.g., swingably) connected with respect to the body 11, and includes a sensor unit 13 at an end opposite to an end where the body 11 is disposed. The sensor unit 13 is insertable into the mouth. Moreover, the end of the measurement unit 12 opposite to the end where the sensor unit 13 is disposed is disposed inside the body 11. The flow stopper 14 has a surface with a curvature different from a curvature of the surface of the measurement unit 12, and is disposed between the measurement unit 12 and the body 11.

As shown in FIG. 2, the flow stopper 14 having a surface with a curvature different from a curvature of the surface of the measurement unit 12 is disposed between the measurement unit 12 and the body 11. Thus, also when the oral tool 10 is removed from the mouth, saliva of a subject less easily flows toward the body of the oral tool 10 gripped by a measuring operator, and the oral tool 10 is thus hygienic.

Components in the oral tool 10 will now be described.
Body

Figure 4:
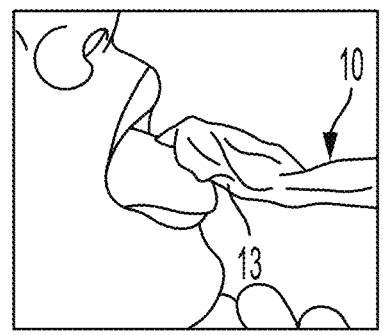
FIG. 4 is a schematic diagram of a sensor unit while being in contact with the tongue.

The body 11 is a member mainly held by the hand. For example, as shown in FIG. 1, the body 11 may include a finger mount 15 on which the finger is placed when held. The body 11 includes a main circuit board 21 that controls measurement of the oral tool 10, and a mechanical switch 17 that is configured to switch between a no-measurement mode and a measurement mode. Moreover, the main circuit board 21 and the mechanical switch 17 are connected to each other. As illustrated in FIG. 3, the body 11 and the measurement unit 12 are connected to a joint 20 with the flow stopper 14 interposed therebetween. The body 11 may have a length of 5 mm to 20 mm in the x direction according to an exemplary aspect.
Measurement Unit FIG. 4 is a schematic diagram of the sensor unit 13 brought into contact with the tongue.

As described above, the measurement unit 12 is disposed swingably with respect to the body 11. For example, as illustrated in FIG. 3, the measurement unit 12 may extend in the −x direction from the body 11, and can be constructed to be moveable (e.g., swingable) about a swing rotation shaft 23 in the vertical direction (i.e., in the z direction) perpendicular to the x direction or the extension direction, or swingable up and down. Here, the measurement unit 12 swings in a zx plane. Instead of the vertical direction (i.e., in the z direction), the swing direction of the measurement unit 12 may be a horizontal direction (i.e., in the y direction). While swinging in the horizontal direction, the measurement unit 12 swings in a xy plane.

According to an exemplary aspect, the measurement unit 12 can have a length of 5 mm to 10 mm in the extension direction (i.e., in the x direction).

Moreover, the measurement unit 12 includes the sensor unit 13 insertable into the mouth at the end opposite to the end where the body 11 is disposed. The measurement unit 12 may include an oscillator circuit board 22 connected to the sensor unit 13. The sensor unit 13 may be, for example, a sensor board for measuring the moisture of the tongue. For example, the sensor unit 13 may be brought into contact with the tongue, and the measurement unit 12 may swing upward (i.e., in the z direction).

As illustrated in the cross-sectional view in FIG. 3, the measurement unit 12 may include multiple components including, besides the sensor unit 13 and the swing rotation shaft 23, a lower member being in contact with the mechanical switch 17 on the body 11, and an upper member protecting the components including the oscillator circuit board 22.

As further shown, the measurement unit 12 has a shape gradually thickened in the extension direction toward the body 11 from the end where the sensor unit 13 is disposed. Preferably, the ratio of the thickness of the measurement unit 12 where the flow stopper 14 is disposed to the thickness of the flow stopper 14 falls within the range of 1:1 to 1:2. The measurement unit 12 with this shape has a thin distal end to be easily insertable into the mouth. The thick body 11 is constructed to be easily grippable by the hand, and thus enables uniform application of a load on a measurement target without causing excessive stress.

The distal end of the measurement unit 12 including the sensor unit 13 is to be inserted into the mouth, and thus has a thickness of smaller than or equal to 15 mm in the vertical direction.

For example, as shown in FIG. 4, the sensor unit 13 can be configured to may start a measurement using the mechanical switch 17 that starts a measurement upon receipt of a specific load, for example, when the sensor unit 13 is brought into contact with the tongue. The mechanical switch 17 can be constructed to be mechanically pressed in the no-measurement mode or a stand-by state, and may be opened in the measurement mode or a measurement state. The mechanical switch 17 may be pressed and urged by an elastic member such as a spring in the no-measurement mode, and opened with the elastic member such as a spring being pushed upward in the measurement mode. Thus, in response to the pressure from the tongue pressed against the sensor unit 13 exceeding a specific load, the measurement unit 12 levels out to open the mechanical switch 17, and to be ready to start a measurement. Here, the elastic member controls the load that urges downward the sensor unit 13 at the distal end of the measurement unit 12.

Figure 5A:
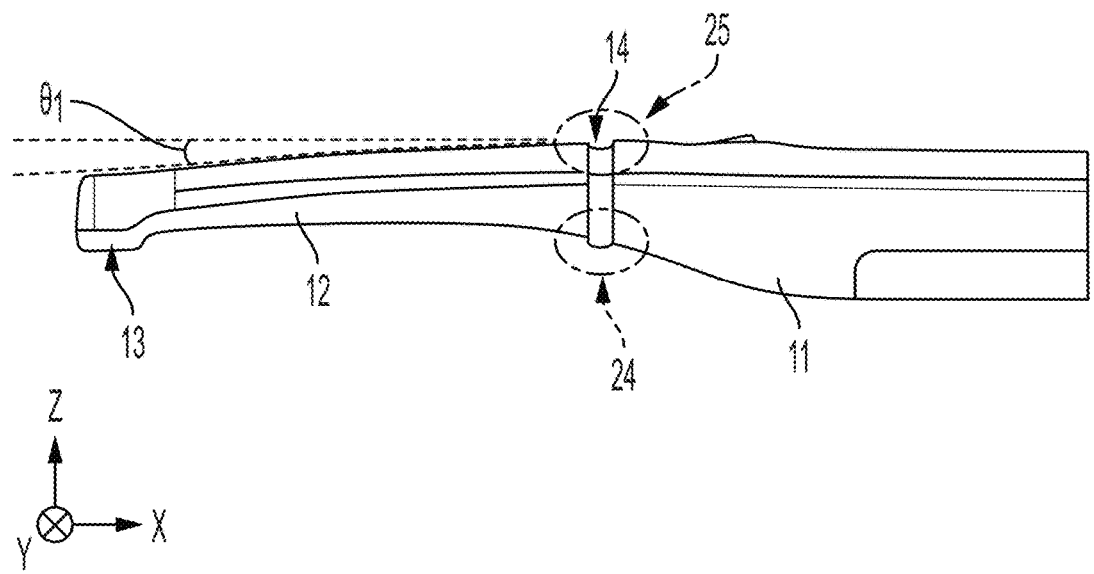
FIG. 5A is a schematic diagram of the vertical position of the flow stopper of the oral tool in a no-measurement mode.

In the no-measurement mode (e.g., a stand-by state) illustrated in FIG. 5A, assuming that the upper surface of the body 11 is a horizontal plane, the distal end of the measurement unit 12 extends at an angle of inclination $\theta_1$ of approximately 3 degrees downward (i.e., in the −z direction) with respect to the horizontal plane. On the other hand, in the measurement mode (e.g., a measurement state) illustrated in FIG. 6A, the distal end of the measurement unit 12 extends along the horizontal plane.

In the no-measurement mode, the measurement unit 12 is inclined downward with respect to the horizontal plane. When the sensor unit 13 is brought into contact with the tongue to swing the measurement unit 12 upward (i.e., in the z direction), the measurement unit 12 levels out. Thus, the mechanical switch 17 is opened, and the measurement unit 12 enters the measurement mode to start a measurement.

In contrast, the mechanical switch 17 may be opened in the no-measurement mode or the stand-by state, and mechanically pressed in the measurement mode or the measurement state.

Flow Stopper

As illustrated in FIG. 1 and FIG. 2, the flow stopper 14 is disposed at the boundary between the body 11 and the measurement unit 12. For example, the flow stopper 14 can be disposed throughout the boundary between the body 11 and the measurement unit 12. In the exemplary aspect, the flow stopper 14 can have an annular shape when viewed in the x direction. A width d1 of the flow stopper 14 at the boundary between the body 11 and the measurement unit 12 is, for example, 2 mm to 20 mm. This configuration can reduce abrasion resulting from collision of outer covers of the body 11 and the measurement unit 12 at the boundary. This configuration can also at least partially prevent saliva from flowing from the measurement unit 12 throughout the outer circumference.

As illustrated in FIG. 2, a gap 16 may be left between the measurement unit 12 and the flow stopper 14. The gap 16 has a distance d2 of, for example, 0.05 mm to 5 mm. The existence of the gap 16 can at least partially prevent saliva from flowing from the measurement unit 12 toward the body 11.

Moreover, according to the exemplary aspect, the flow stopper 14 includes a surface with a curvature different from a curvature of the surface of the measurement unit 12. Thus, also when the oral tool 10 is removed from the mouth, saliva of a subject less easily flows toward the body of the oral tool gripped by a measuring operator, and the oral tool 10 is thus hygienic.

The flow stopper 14 can be formed from a deformable soft member. Moreover, the flow stopper 14 can be deformed in accordance with movement of the measurement unit 12. When not deformed, the flow stopper 14 may be entirely or partially covered. In contrast, during use, the flow stopper 14 is deformed as appropriate, and at least partially prevents saliva from flowing toward the body with the surface with a curvature different from a curvature of the surface of the measurement unit 12.

In the exemplary aspect, the flow stopper 14 is, for example, a soft member, and can be formed from, for example, natural rubber, styrene-butadiene rubber (SBR), chloroprene rubber (CR), acrylonitrile rubber (NBR), butyl rubber (IIR), ethylene-propylene rubber (EPDM), silicone rubber, or thermoplastic polyurethane (TPU) (or called polyurethane rubber (U)). Silicone rubber and thermoplastic polyurethane (TPU) are particularly preferable. In general, these materials less easily hydrolyze, have static physical properties, and are thus durable in long-term use.

Figure 5B:
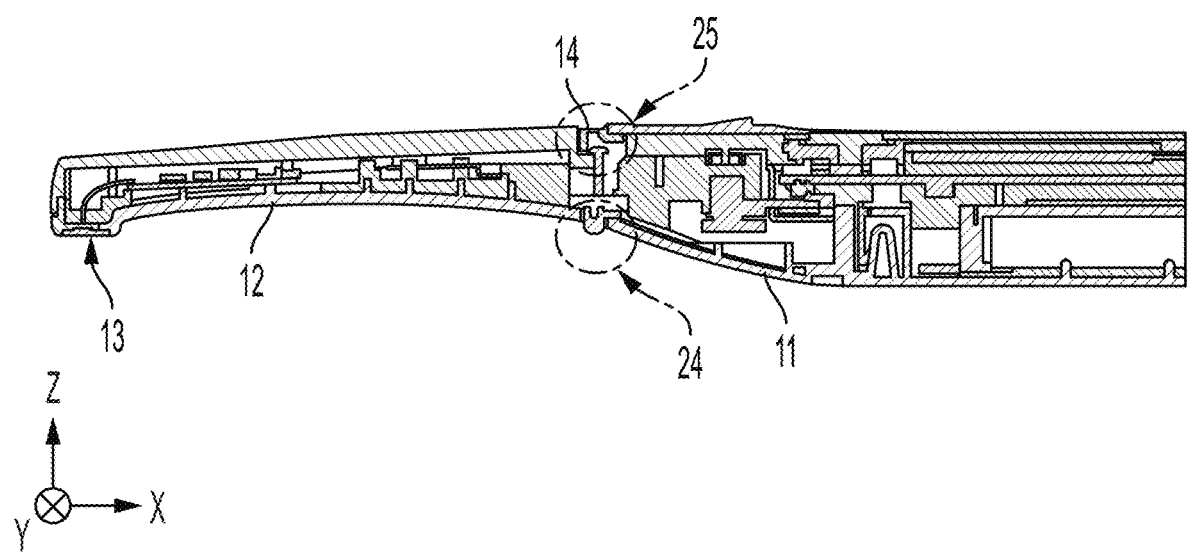
FIG. 5B is a schematic cross-sectional view of the cross-sectional structure of the oral tool in the no-measurement mode shown in FIG. 5A.
Figure 6A:
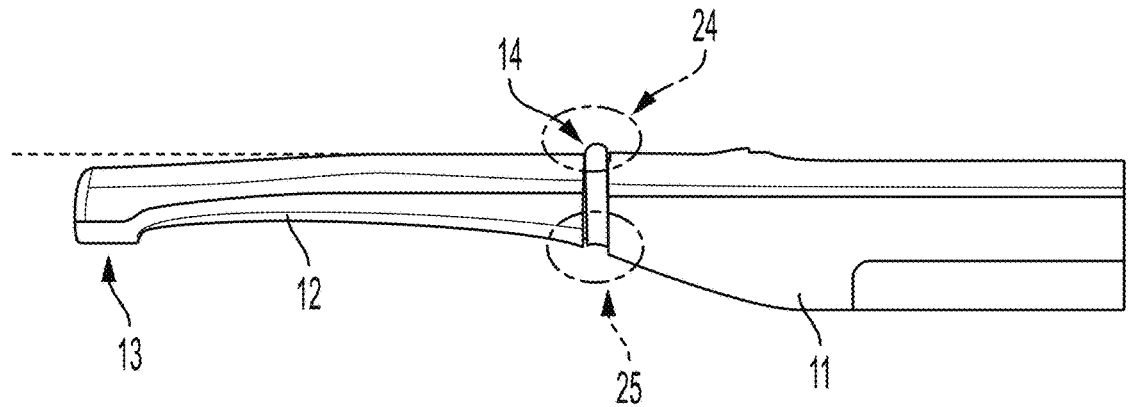
FIG. 6A is a schematic diagram of the vertical position of the flow stopper of the oral tool in a measurement mode.
Figure 6B:
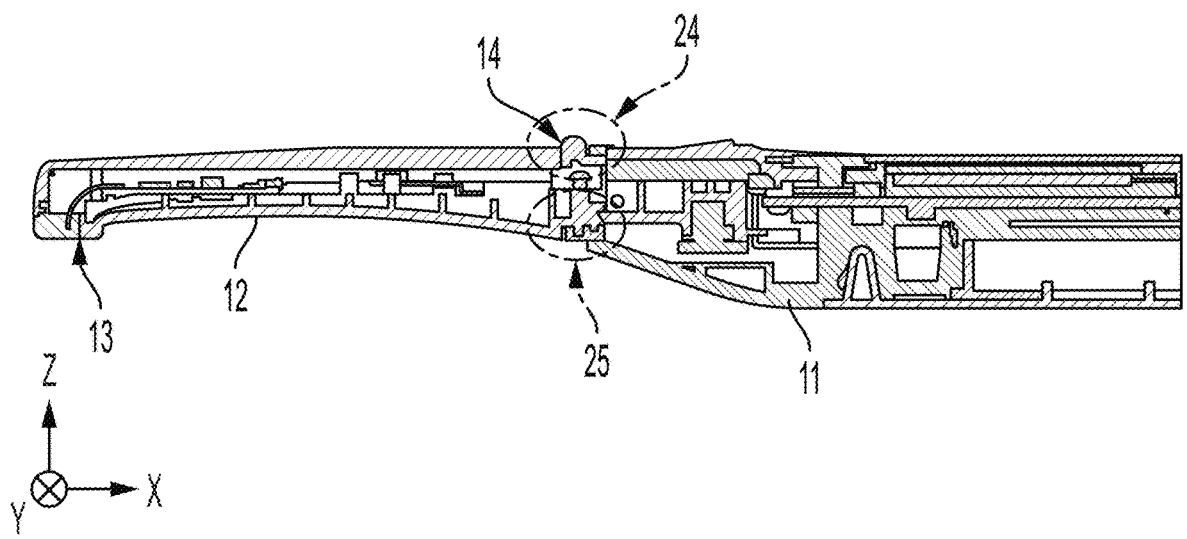
FIG. 6B is a schematic cross-sectional view of a cross-sectional structure of the oral tool in the measurement mode shown in FIG. 6A.

FIG. 5A is a schematic diagram of the vertical position of the flow stopper 14 of the oral tool 10 in the no-measurement mode. FIG. 5B is a schematic cross-sectional view of the cross-sectional structure of the oral tool 10 in the no-measurement mode shown in FIG. 5A. FIG. 6A is a schematic diagram of the vertical position of the flow stopper 14 in the oral tool 10 in a measurement mode. FIG. 6B is a schematic cross-sectional view of a cross-sectional structure of the oral tool 10 in the measurement mode shown in FIG. 6A.

In the no-measurement mode, the measurement unit 12 is held while being inclined downward. As illustrated in FIG. 5A and FIG. 5B, in the no-measurement mode, the flow stopper 14 at the boundary between the body 11 and the measurement unit 12 is pressed by the measurement unit 12 to form a convex protrusion 24 protruding outward at the lower portion of the boundary. At the upper portion of the boundary, on the other hand, the flow stopper 14 is pulled by the measurement unit 12 to form a concave recess 25.

In the measurement mode, the measurement unit 12 is horizontally held. As illustrated in FIG. 6A and FIG. 6B, in the measurement mode, the flow stopper 14 at the boundary between the body 11 and the measurement unit 12 is pressed by the measurement unit 12 to form a convex protrusion 24 protruding outward at the upper portion of the boundary. At the lower portion of the boundary, on the other hand, the flow stopper 14 is pulled by the measurement unit 12 to form a concave recess 25.

As described above, in either the no-measurement mode or the measurement mode, the flow stopper 14 disposed at the boundary between the body 11 and the measurement unit 12 is deformed to form the convex protrusion 24 or the concave recess 25 and reduce the stress. The protrusion 24 or the recess 25 can at least partially prevent flow of saliva from the measurement unit 12.

Stopper

As described above, the measurement unit 12 swings vertically about the rotation shaft 23. On the other hand, the joint 20 at the boundary between the body 11 and the measurement unit 12 and the surroundings of the mechanical switch 17 function as a stopper mechanism that reduces the swing of the measurement unit 12.

First Modification of the Exemplary Aspect
Flow Stopper Including Guard

Figure 7:
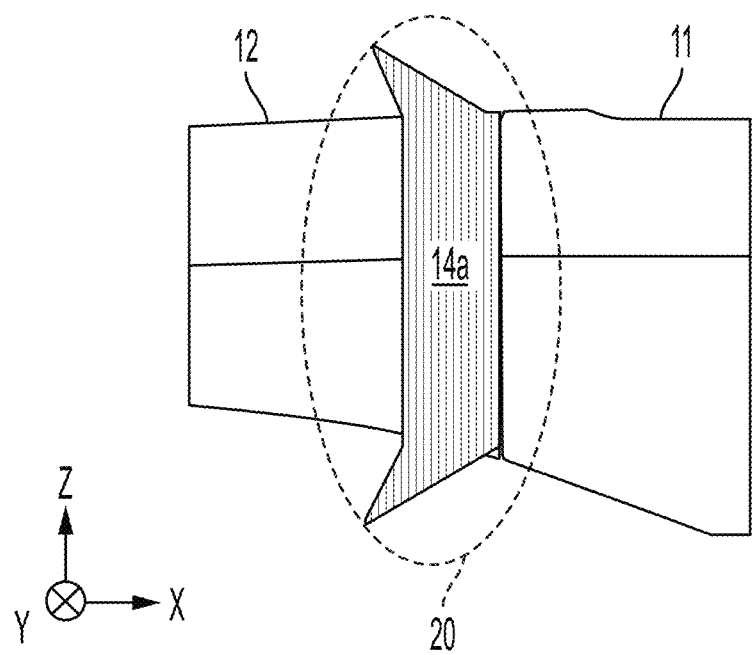
FIG. 7 is a schematic diagram showing a flow stopper including a guard at a joint in an oral tool according to a first modification of the exemplary embodiment.

FIG. 7 is a schematic diagram of a flow stopper including a guard at the joint 20 of an oral tool according to a first modification of the exemplary aspect.

In the oral tool according to the first modification, a flow stopper 14a can include a guard at the joint 20, which is a boundary between the body 11 and the measurement unit 12. In an exemplary aspect, the guard can have a shape of, for example, an Elizabethan collar used for treatment of animals such as cats. This structure can stop saliva of a subject with the guard, and thus at least partially prevent saliva from flowing toward the body of the oral tool gripped by a measuring operator.

Second Modification of the Exemplary Aspect
Longitudinal Ribs at Joint

Figure 8:
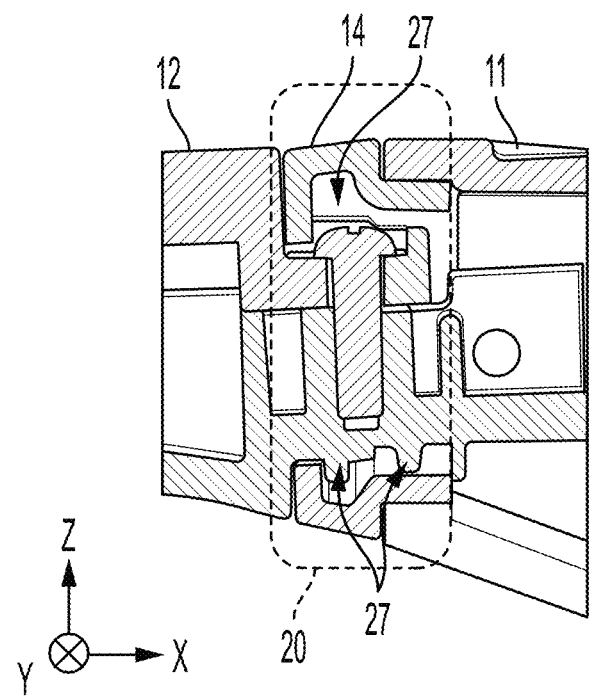
FIG. 8 is a cross-sectional view of longitudinal ribs in the cross-sectional structure at a joint in an oral tool according to a second modification of the exemplary embodiment.

FIG. 8 is a cross-sectional view of longitudinal ribs 27 in the cross-sectional structure at the joint 20 of the oral tool according to a second modification of the exemplary aspect.

In the oral tool according to the second modification, the joint 20 at the boundary between the body 11 and the measurement unit 12 may include, for example, the longitudinal ribs 27 disposed adjacent to the flow stopper 14 and having a convex shape protruding in the direction (i.e., in the z direction) in which the measurement unit 12 swings. The measurement unit 12 or the body 11 adjacent to the flow stopper 14 including the longitudinal ribs 27 protruding in the swing direction acts against the stress for contracting in the horizontal direction (i.e., in the x direction). In addition, the longitudinal ribs 27 can be constructed to prevent excessive warpage of the flow stopper 14 in the annular shape and allows the flow stopper 14 to be appropriately deformed. The longitudinal ribs 27 can also be disposed at either the body 11 or the measurement unit 12 at the joint 20.

This structure at least partially prevents saliva of a subject from flowing toward the body of the oral tool gripped by a measuring operator.

In general, it is noted that the present disclosure includes appropriate combinations of any two or more of the above-described embodiments or examples, and can achieve effects of the respective embodiments or examples.

An oral tool according to exemplary embodiments of the present invention includes a flow stopper disposed between a measurement unit and a body and having a surface with a curvature different from a curvature of the surface of the measurement unit. Thus, also when the oral tool is removed from the mouth, saliva of a subject less easily flows toward the body of the oral tool gripped by a measuring operator, and the oral tool is thus hygienic. This oral tool is thus useful as a medical device.

While the exemplary embodiments of the invention have been described above, it is to be understood that variations and modifications will be apparent to those skilled in the art without departing from the scope and spirit of the invention.

What is claimed:

1. An oral tool, comprising:
    a body;
    a measurement unit connected to the body and including a sensor unit disposed at an end opposite to an end where the measurement unit is connected to the body; and
    a flow stopper disposed between the measurement unit and the body, wherein the flow stopper has a surface with a curvature that is different than a curvature of a surface of the measurement unit, and
    wherein the flow stopper is disposed at a boundary between the body and the measurement unit and is constructed to be deformed to form one of a convex protrusion or a concave recess.

2. The oral tool according to claim 1, wherein the respective surfaces of the flow stopper and the measurement unit are outer surfaces that are disposed in respective positions continuous to each other.

3. The oral tool according to claim 1, wherein the flow stopper comprises a water-repellent member.

4. The oral tool according to claim 1, wherein the flow stopper comprises a deformable soft member.

5. The oral tool according to claim 4, wherein the flow stopper is constructed to be deformed in response to a movement of the measurement unit relative to the body.

6. The oral tool according to claim 1, wherein the flow stopper comprises a shape of a guard that faces toward the measurement unit.

7. The oral tool according to claim 1, wherein the flow stopper is spaced by a gap from one of the measurement unit or the body.

8. The oral tool according to claim 1, wherein the flow stopper comprises a material selected from a group consisting of natural rubber, styrene-butadiene rubber, chloroprene rubber, acrylonitrile rubber, butyl rubber, ethylene-propylene rubber, silicone rubber, and thermoplastic polyurethane.

9. The oral tool according to claim 1, wherein the flow stopper comprises a convex or concave shape to extend along a circumference of a portion between the measurement unit and the body.

10. The oral tool according to claim 1, wherein the flow stopper is constructed as a buffer member between the body and the measurement unit.

11. The oral tool according to claim 10, wherein at least one of the body and the measurement unit includes a protruding longitudinal rib that is in direct contact with the flow stopper.

12. The oral tool according to claim 1, wherein the sensor unit is configured to be inserted into a mouth of a subject and the sensor comprises a sensor board configured to measure a moisture in the mouth.

13. The oral tool according to claim 1, wherein the measurement unit is constructed to move relative to the body about a swing rotation shaft.

14. An oral tool, comprising:
    a body;
    a measurement unit connected to the body and moveable relative to the body where the measurement unit connect to the body;
    a sensor unit disposed at an end of the measurement unit opposite the body; and
    a flow stopper disposed between the measurement unit and the body,
    wherein with the flow stopper has an outer surface with a curvature that is different than a curvature of an outer surface of the measurement unit that is adjacent to the flow stopper, and
    wherein the flow stopper is disposed at a boundary between the body and the measurement unit and is constructed to be deformed to form one of a convex protrusion or a concave recess.

15. The oral tool according to claim 14, wherein the flow stopper is constructed to be deformed in response to a movement of the measurement unit relative to the body.

16. The oral tool according to claim 14, wherein the flow stopper comprises a shape of a guard that faces toward the measurement unit.

17. The oral tool according to claim 14, wherein the flow stopper is spaced by a gap from one of the measurement unit or the body.

18. The oral tool according to claim 14, wherein the flow stopper comprises a material selected from a group consisting of natural rubber, styrene-butadiene rubber, chloroprene rubber, acrylonitrile rubber, butyl rubber, ethylene-propylene rubber, silicone rubber, and thermoplastic polyurethane.

* * * * *